United States Patent
Manzke et al.

(10) Patent No.: US 10,825,358 B2
(45) Date of Patent: Nov. 3, 2020

(54) CLINICAL DECISION SUPPORT AND TRAINING SYSTEM USING DEVICE SHAPE SENSING

(71) Applicant: KONINKLIJKE PHILIPS N.V., Eindhoven (NL)

(72) Inventors: Robert Manzke, Bönebüttel (DE); Raymond Chan, San Diego, CA (US); Bharat Ramachandran, Morganville, NJ (US); Michael Chun-chieh Lee, Lexington, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 593 days.

(21) Appl. No.: 14/428,658

(22) PCT Filed: Sep. 20, 2013

(86) PCT No.: PCT/IB2013/058686
§ 371 (c)(1),
(2) Date: Mar. 17, 2015

(87) PCT Pub. No.: WO2014/053940
PCT Pub. Date: Apr. 10, 2014

(65) Prior Publication Data
US 2015/0255004 A1    Sep. 10, 2015

Related U.S. Application Data

(60) Provisional application No. 61/708,220, filed on Oct. 1, 2012.

(51) Int. Cl.
*G09B 23/28*    (2006.01)
*G16H 50/50*    (2018.01)
(Continued)

(52) U.S. Cl.
CPC .......... *G09B 23/28* (2013.01); *G06F 19/325* (2013.01); *G09B 5/02* (2013.01); *G09B 23/285* (2013.01);
(Continued)

(58) Field of Classification Search
CPC ...... G06F 19/00; G06F 19/321; G06F 19/325; G06F 19/3437; G06F 19/345;
(Continued)

(56) References Cited

U.S. PATENT DOCUMENTS 6,563,107 B2 *    5/2003    Danisch ................ G01B 11/18
                                                              250/227.14
7,734,077 B2    6/2010    Hirsch et al.
(Continued)

FOREIGN PATENT DOCUMENTS

CN    101996507 A    3/2011
JP    2004223128 A    8/2004
(Continued)

OTHER PUBLICATIONS

Liu, H., Farvardin, A., Pedram, S. and Iordachita I., "Large Deflection Shape Sensing of a Continuum Manipulator for Minimally-Invasive Surgery," IEEE Int Conf Robot Autom. 2015; May 26, 2015; 201-206, https://www.ncbi.nlm.nih.gov/pmc/articles/PMC4547476/, abstract.

*Primary Examiner* — Michael C Grant

(57) ABSTRACT

A training or rating system includes a shape sensing enabled device (104) and a database (140) of possible shapes and sequences of shapes for the shape sensing enabled device. The possible shapes and sequences of shapes include a collection of poses derived by appropriately performing a procedure with the shape sensing enabled device. A comparison module (154) is configured to compare real-time poses of the shape sensing enabled device with the collec-
(Continued)

tion of poses in the database to output comparison feedback for a user of the shape sensing enabled device.

22 Claims, 4 Drawing Sheets

(51) Int. Cl.
G16H 50/20 (2018.01)
G06F 19/00 (2018.01)
G09B 5/02 (2006.01)

(52) U.S. Cl.
CPC .............. *G16H 50/20* (2018.01); *G16H 50/50* (2018.01); *G06F 19/321* (2013.01)

(58) Field of Classification Search
CPC ... G06F 19/3481; G06B 23/28; G06B 23/285; A61B 2034/256; A61B 2034/2061; A61B 2034/107; A61B 34/20; A61B 34/25; A61B 5/065
USPC ........................................................ 434/267
See application file for complete search history.

(56) References Cited

U.S. PATENT DOCUMENTS

| 8,391,571 | B2 | 3/2013 | Cinquin et al. |
| 8,403,675 | B2 | 3/2013 | Stoianovici et al. |
| 8,449,301 | B2 | 5/2013 | Cyr et al. |
| 9,196,176 | B2 | 11/2015 | Hager et al. |
| 2005/0142525 | A1* | 6/2005 | Cotin ................. G09B 23/285 434/262 |
| 2005/0277096 | A1 | 12/2005 | Hendrickson et al. |
| 2006/0234195 | A1 | 10/2006 | Grund-Pedersen et al. |
| 2006/0264742 | A1* | 11/2006 | Neubauer ............. A61B 34/20 600/424 |
| 2007/0135803 | A1 | 6/2007 | Belson |
| 2007/0172803 | A1* | 7/2007 | Hannaford ........... G09B 23/285 434/262 |
| 2008/0097159 | A1* | 4/2008 | Ishiguro ............... A61B 1/0051 600/145 |
| 2008/0212082 | A1* | 9/2008 | Froggatt ............. G01M 11/083 356/73.1 |
| 2008/0235052 | A1 | 9/2008 | Node-Langlois et al. |
| 2009/0202972 | A1 | 8/2009 | Adhami et al. |
| 2010/0056904 | A1 | 3/2010 | Saunders et al. |
| 2010/0099951 | A1* | 4/2010 | Laby .................. A61B 1/0052 600/144 |
| 2010/0249506 | A1* | 9/2010 | Prisco ................ A61B 1/00009 600/117 |
| 2011/0046476 | A1* | 2/2011 | Cinquin ............... G09B 23/285 600/424 |
| 2011/0319714 | A1* | 12/2011 | Roelle ................ A61B 1/00006 600/118 |
| 2013/0303892 | A1* | 11/2013 | Zhao ..................... A61B 5/061 600/424 |

FOREIGN PATENT DOCUMENTS

| JP | 2007233850 | A | 9/2007 |
| JP | 2008229332 | A | 10/2008 |
| WO | 9630885 | A1 | 10/1996 |
| WO | 2004051604 | A1 | 6/2004 |
| WO | 2009049038 | A1 | 4/2009 |
| WO | 2011108994 | A1 | 9/2011 |
| WO | 2011141830 | A1 | 11/2011 |
| WO | 2012065175 | A2 | 5/2012 |
| WO | 2012095784 | A1 | 7/2012 |
| WO | 2012101555 | A1 | 8/2012 |
| WO | 2012106706 | A2 | 8/2012 |

* cited by examiner

CLINICAL DECISION SUPPORT AND TRAINING SYSTEM USING DEVICE SHAPE SENSING

CROSS-REFERENCE TO PRIOR APPLICATIONS

This application is the U.S. National Phase application under 35 U.S.C. § 371 of International Application Serial No. PCT/IB2013/058686, filed on Sep. 20, 2013, which claims the benefit of U.S. Application Ser. No. 61/708,220, filed on Oct. 1, 2012. These applications are hereby incorporated by reference herein.

BACKGROUND

Technical Field

This disclosure relates to medical instruments and systems and more particularly to systems and method which employ shape sensing information for training and decision making in medical and other applications.

Description of the Related Art

In medical procedures, skill level and experience of a physician generally dictates clinical efficiency and efficacy of the procedure. This creates a bias in favor of experienced physicians over fellows who are inexperienced, resulting, eventually, in patients and hospital administrators preferring and opting for the physicians with higher experience. In many instances, this bias can be overcome by the proper training of less experienced physicians.

SUMMARY

In accordance with the principles of the present invention, a training or rating system is provided which includes a shape sensing enabled device and a database of possible shapes and sequences of shapes for the shape sensing enabled device. The possible shapes and sequences of shapes include a collection of poses derived by appropriately performing a procedure with the shape sensing enabled device. A comparison module can be configured to compare real-time poses of the shape sensing enabled device with the collection of poses in the database to output comparison feedback for a user of the shape sensing enabled device.

The database can include data collected from one or more experts appropriately performing the procedure. The shape sensing enabled device can include an optical fiber shape sensing device or an electromagnetically tracked device. Additionally, the database can include a best practices database, which can include procedure specific constraints or environment specific constraints. It is also possible that database includes libraries of data related to a procedure type, a physician and a particular circumstance for the procedure.

Further, the system can comprise a guidance system configured to provide information to a user to assist the user in determining a course of action during the procedure. The information of the guidance system can be based upon the collection of poses derived by appropriately performing the procedure. The database can store the collection of poses associated with procedure outcomes such that the comparison feedback includes a probable outcome of the procedure performed by the user. The comparison feedback can include a comparison of execution times for procedure steps, and the comparison feedback can include a rating of the user.

Also in accordance with the principles of the present invention, a decision support system is provided which includes a shape sensing enabled device and a database of possible shapes and sequences of shapes for the shape sensing enabled device. The possible shapes and sequences of shapes include a collection of poses derived by appropriately performing a procedure with the shape sensing enabled device. A comparison module can be configured to compare real-time poses of the shape sensing enabled device with the collection of poses in the database to output comparison feedback to a user of the shape sensing enabled device. A guidance module can be configured to provide information to a user to assist the user in determining a course of action during the procedure.

The database can include data collected from one or more experts appropriately performing the procedure. The shape sensing enabled device can include an optical fiber shape sensing device or an electromagnetically tracked device. Additionally, the database can include a best practices database, which can include procedure specific constraints or environment specific constraints. The database can include libraries of data related to a procedure type, a physician and a particular circumstance for the procedure.

Further, the system can comprise a guidance system having information based upon the collection of poses derived by appropriately performing the procedure. The database can store the collection of poses associated with procedure outcomes such that the comparison feedback includes a probable outcome of the procedure performed by the user to assist in decision making. The comparison feedback can be provided by a feedback mechanism that provides feedback through one or more of visual, acoustic and graphical modes. It is also possible that the comparison feedback includes a warning message for an undesirable action.

Additionally, in accordance with the principles of the present invention, a method for procedural training and/or decision support is provided which includes employing a shape sensing enabled device in simulated or actual conditions; comparing usage of the shape sensing enabled device against a database of possible shapes and sequences of shapes for the shape sensing enabled device, the possible shapes and sequences of shapes including a collection of poses derived by appropriately performing a procedure with the shape sensing enabled device; and outputting a rating or improvement feedback based on a comparison of real-time poses of the shape sensing enabled device with the collection of poses in the database.

The method can further include training the database using data collected from one or more experts appropriately performing the procedure. The shape sensing enabled device can include an optical fiber shape sensing device or an electromagnetically tracked device. The method can further include creating a best practices database, which can include procedure specific constraints or environment specific constraints employed in the step of outputting. The database can include libraries of data related to a procedure type, a physician and a particular circumstance for the procedure. The method can further include providing information to a user to assist the user in determining a course of action during the procedure. The information can be based upon the collection of poses derived by appropriately performing the procedure. It is also possible that the method further includes warning the user of an undesirable action during the procedure. Additionally, the outputting can include outputting a probable outcome of the procedure performed by the user, and the feedback can include a comparison of execution times for procedure steps. Moreover, the method can further include certifying a user based on performance feedback.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

Figure 1:
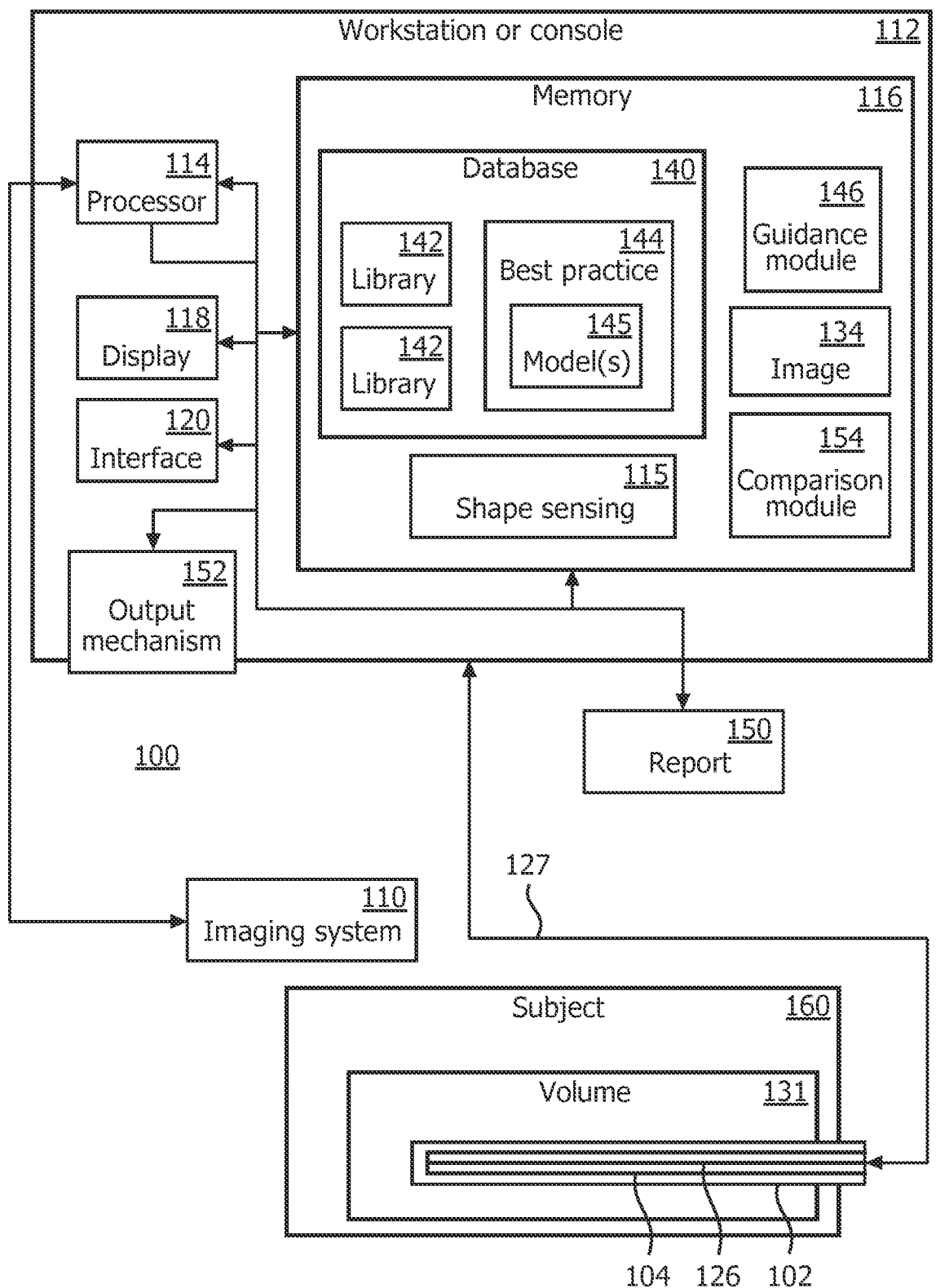
FIG. 1 is a block/flow diagram showing a training and/or decision support system which employs shape sensing in accordance with one embodiment.

In accordance with the present principles, medical devices, such as guidewires or catheters, may be combined with shape sensing technology to collect information for training models and training tools. Through the use of shape sensing technology, the determination of location and shape of the medical device at any instance of time during a procedure is possible. Clinical decision support (CDS) and advanced procedure training systems can help to improve this situation and promote evidence-based approaches. The present principles provide a system that employs data derived in combination with a shape sensing enabled device to create best practice guidelines to actuate the device to get a clinical result, e.g. guiding the devices into a specific anatomy or deploying an implant. Best practice guidelines may be adhered to by monitoring the actuation steps of a trained or experienced physician to reach an anatomical feature or location or deploy an implant or object within a body.

The training system may take the form of a CDS system and may obtain real-time feedback/reporting on a probability of success of the procedure, e.g., by predicting clinical outcomes based on the accessibility of the anatomy of interest obtained from a shape or changes that the device has undergone during manipulation in the procedure itself. Other features include deriving real-time road-mapping suggestions from the CDS system pertaining to optimal next steps in the delivery of the instrument or therapy to a target based on a training library of similar clinical cases with corresponding instrument-manipulation archive recordings and clinical outcomes.

The present embodiments may be employed to comparatively demonstrate advantages in performing a procedure in a certain way. For example, the system can, in combination with a database having a certain regime of procedures, demonstrate the comparative advantage of one technique over another based on comparison of metrics such as dose, time, and success rate between procedure groups.

Dynamic shape data and derivative measures available in a database may be employed to train physicians on how to manipulate a device to achieve a desired clinical effect or to improve a measured metric (e.g., reduce time or trauma, etc.). The shape data can be obtained using a number of tracking technologies, including but not limited to optical shape sensing, electromagnetic tracking or other localization/tracking system, where multiple sensors are employed to track a part of or the entire device.

It should be understood that the present invention will be described in terms of medical instruments and procedures; however, the teachings of the present invention are much broader and are applicable to any procedure where training is beneficial. In some embodiments, the present principles are employed in tracking or analyzing complex biological or mechanical systems. In particular, the present principles are applicable to internal tracking procedures of biological systems, procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Referring now to the drawings in which like numerals represent the same or similar elements and initially to FIG. 1, a system 100 for training/rating or providing decision support for medical personal in performing one or more procedures is illustratively shown in accordance with one embodiment. System 100 may include a workstation or console 112 from which a procedure is supervised and/or managed. Workstation 112 preferably includes one or more processors 114 and memory 116 for storing programs and applications. While the system 100 may be configured to work with different shape sensing technologies (e.g., electromagnetic (EM) tracking, etc.), optical fiber sensing will be illustratively described. In this embodiment, memory 116 may store a shape sensing module 115 configured to interpret feedback signals from a shape sensing device or system 104. Sensing module 115 is configured to use optical signal feedback (and any other feedback, e.g., EM tracking) to reconstruct deformations, deflections and other changes associated with a medical device or instrument 102 and/or its surrounding region. The medical device 102 may include a catheter, a guidewire, a probe, an endoscope, a robot, an electrode, a filter device, a balloon device, or other medical component, etc.

The shape sensing system 104 may be employed in a subject 160, which may include an anatomical training model, a living body, a cadaver or a simulated subject using virtual models and simulated virtual guidance responsive to manual manipulations of the device 104.

The shape sensing system 104 on device 102 includes one or more optical fibers 126 which are coupled to the device 102 in a set pattern or patterns. The optical fibers 126 connect to the workstation 112 through cabling 127. The cabling 127 may include fiber optics, electrical connections, other instrumentation, etc., as needed.

Shape sensing system 104 with fiber optics may be based on fiber optic Bragg grating sensors. A fiber optic Bragg grating (FBG) is a short segment of optical fiber that reflects particular wavelengths of light and transmits all others. This is achieved by adding a periodic variation of the refractive index in the fiber core, which generates a wavelength-specific dielectric mirror. A fiber Bragg grating can therefore be used as an inline optical filter to block certain wavelengths, or as a wavelength-specific reflector.

A fundamental principle behind the operation of a fiber Bragg grating is Fresnel reflection at each of the interfaces where the refractive index is changing. For some wavelengths, the reflected light of the various periods is in phase so that constructive interference exists for reflection and, consequently, destructive interference for transmission. The Bragg wavelength is sensitive to strain as well as to temperature. This means that Bragg gratings can be used as sensing elements in fiber optical sensors. In an FBG sensor, the strain causes a shift in the Bragg wavelength.

One advantage of this technique is that various sensor elements can be distributed over the length of a fiber. Incorporating three or more cores with various sensors (gauges) along the length of a fiber that is embedded in a structure permits a three dimensional form of such a structure to be precisely determined, typically with better than 1 mm accuracy. Along the length of the fiber, at various positions, a multitude of FBG sensors can be located (e.g., 3 or more fiber sensing cores). From the strain measurement of each FBG, the curvature of the structure can be inferred at that position. From the multitude of measured positions, the total three-dimensional form is determined.

As an alternative to fiber-optic Bragg gratings, the inherent backscatter in conventional optical fiber can be exploited. One such approach is to use Rayleigh scatter in standard single-mode communications fiber. Rayleigh scatter occurs as a result of random fluctuations of the index of refraction in the fiber core. These random fluctuations can be modeled as a Bragg grating with a random variation of amplitude and phase along the grating length. By using this effect in three or more cores running within a single length of multi-core fiber, the 3D shape and dynamics of the surface of interest can be followed.

The system 100 may be employed to record historical data during a procedure to build a database 140 of device 102 movements that are associated with outcomes of the procedure. In this sense, system 100 functions in a training mode to train the database 140 to accumulate comparative data that can be employed later to rate performance of individual users in a training environment or provide guidance to physicians during a procedure. The database 140 may include libraries 142 of performance data of other physicians or of a particular physician (e.g., a most prominent or proficient physician or a highest rated physician). The data may be categorized based upon the procedure, particular patient or environmental circumstances, etc. Dynamic shape data available in the database 140 may be used to train physicians to manipulate the device 102 to achieve a desired clinical effect. The data stored in the libraries and related databases may include the dynamic shape data, that is, a series of points representing the spatial and temporal coordinates of segments of the device within a given reference frame. In particular, given a labeling of equidistant points along the length of the device 102 in its fully relaxed position (i.e. in a straight line, in the case of simple fiber), each of these labeled points can be tracked as an (x, y, z, t) coordinate specifying the position (x,y,z) of that particular element within the instrument at a given time t in the procedure, where x,y,z are given in a pre-defined reference frame. Equivalently, the libraries 142 may store the excursions of each of these labeled points from their previous positions, beginning at time t=0 with no excursions, and then subsequently measuring the delta-x, delta-y, and delta-z at each new time point t. It is understood that other equivalent approaches to storing this data are possible, with the overall goal of being able to determine the pose of the instrument at any particular point in time.

Moreover, the databases 140 (and libraries 142, etc.) described here may be augmented with metadata describing the procedures, including the operating physician, demographic information about the patient and his or her conditions, description of the planned procedure, time length of the procedure, amount of radiation used, types of equipment employed, radiological images of the patient, and the like. These databases 140 may be further augmented with information about the outcome of the procedure or outcome of the patient, such as disease free survival, complications, amount of required recovery time and/or medications, and the like.

A best practice database 144 may be provided that may or may not be integrated with the database 140. The best practices database 144 may include best surgical practice general guidelines, hospital or local guidelines, patient-related preference or circumstances, etc. The best practice database 144 may be employed to store a model or models 145 that encompass a goal or standard which should be achieved for a given procedure. The model 145 may provide tolerances to provide an acceptable range or have multiple performance ranges that can be employed to rate a current performance against a one or more other performances. For example, a certain collection of shapes achieved by the device 102 during a procedure can be compared to the model 145 to determine differences. In one embodiment, the number of different poses or shapes may be compared. In another embodiment, a time or duration of the most significant poses can be compared. In still another embodiment, combinations or sequences of poses or shapes may be compared.

The comparison procedure may be performed by a comparison module 154 computing a metric descriptive of the difference in point positions between the real-time and the stored shape of the object. By way of example, a simple approach would be to first assign either the real-time or the library data (at a given point in time) as the "floating" data set and the other as the "reference" data set, and then roughly align the two shapes by computing rotations, translations, and optionally scaling of the floating data such that the root-mean square distance of points between the floating and reference data sets are minimized, and then using this root-mean square metric as a measure of how well the shapes match at a given time point. Note that the floating or reference data set may be one of the aforementioned "most significant poses". Such approaches can be enhanced by, for example, limiting the analysis to certain portions of a device (a functional end, for example), or conversion to other coordinate systems to reduce the influence of irrelevant motions. Additional enhancements may be achieved by selecting specific procedures from the database for comparison, such as those matching in the previously described metadata. Other comparison methods and techniques are also contemplated.

During procedures other considerations may be dominant, for example, an exposure time to X-rays or chemotherapy. The probable procedure duration and complexity may be compared to determine when X-ray irradiation can be reduced by associating shape or pose sequences that are most likely to reduce expose time and will be clearly superior.

By way of example, best practices may be different depending on the equipment used, the anatomy of the patient, the location of the hospital, the local laws where the surgery is being performed, etc. Other considerations may be programmed and stored in the databases 140 and 144.

In one embodiment, workstation 112 is configured to receive feedback from the shape sensing system 104 and record accumulated position data as to where the shape sensing enabled device 102 has been within the volume 131 during a known procedure. This data can be compared with data stored in the database 140 and/or best practices database 144 to compare the data with past performances of this physician, compare the data to other physicians, groups of physicians or models and to provide metrics or statistics regarding the performance. The comparison may be performed using the comparison module 154. The comparison module 154 employs the stored data in the database(s) 140, 144, and compares the data with the collected data from a current use of the sensing enabled device 102 and/or shape sensing system 104.

Workstation 112 includes a display 118 for viewing internal images of a subject (patient) or volume 131 and may include an image 134 of the shape sensing data as an overlay on real-time or preoperatively recorded images of the volume 131 taken by an imaging system 110. The imaging system 110 may include an X-ray system, computed tomography system, a magnetic resonance system, an ultrasonic system, etc. Other renderings and display techniques are also contemplated. Display 118 may also permit a user to interact with the workstation 112 and its components and functions, or any other element within the system 100. This is further facilitated by an interface 120 which may include a keyboard, mouse, a joystick, a haptic device, or any other peripheral or control to permit user feedback from and interaction with the workstation 112.

Workstation 112 as depicted in FIG. 1 can be employed to handle separate workflows for the same or different purposes. For example, some illustrative workflows may be described as follows. In one envisioned workflow, the database 140 is first created using performances recorded during multiple procedures from experts and experienced physicians and used to create a set of guidelines. These guidelines may include positions of medical devices (as sensed by shapes sensing or other technology), an overall time to perform a procedure or portions of the procedure, time or ability to efficiently achieve an aim or goal of the procedure or a portion thereof, etc. This type of workflow may be employed, e.g., to test medical students and improve the performance of physicians by providing them with necessary feedback that can pinpoint areas of improvement.

Another example of a workflow may include creating a clinical study to prove that a shape sensing based training tool improves the performance of the clinician, reduces a dose (e.g., chemo, drugs, contrast dye or other material that needs to be carefully administered or limited in dose) received, reduces procedure time, etc. In this way, new and more efficient procedures may be developed without operating on or training on a patient. This adds training experience to the clinician while lowering risk.

The system 100 employs device manipulation data in the form of spatiotemporal shapes to record and create best practice guidelines on how to actuate the device 102 to get a clinical result, e.g., guiding it into a specific anatomy or deploying an implantable device. Many metrics may be gathered to determine performance. For example, the amount of time to traverse a portion of the anatomy or the ultimate position of the implantable device may be used. During a recording of the shape, the manipulation steps can be tagged according to the workstep of an interventional procedure. This may be performed during training or during an actual procedure. The tagging or identification of the workstep may be performed manually via data annotation by clinical experts (tags can include graphical, audio, or other quantitative markers in the data record). The tagging may also be performed automatically using a pattern recognition approach. For example, a shape sensing pattern may be compared to patterns in the database 140 to determine when the workstep or poses has been reached based upon a best fit image stored in the database 140 associated with that workstep.

The system 100 may be employed to ensure compliance with best practice guidelines by monitoring the actuation steps of the physician to reach an anatomy or deploy an implantable. Feedback can be provided to the physician during a training session or a procedure in real-time to provide guidance with decision making or to encourage or dissuade the trainee or physician from a particular action.

Each procedure or training session may be scored or rated to provide real-time feedback or report 150 on the probability of success of the procedure, e.g., by predicting clinical outcomes based on the accessibility of the anatomy of interest obtained from shapes the device 102 has undergone during instrument manipulation. The output of the score or rating may be employed to determine if the trainee is now capable of performing a real-life procedure, may be employed for certification or licensing or may be employed for record keeping by an administrator or the like.

The system 100 may also be employed for improving or determining better ways to perform a surgery or procedure. For example, real-time road-mapping suggestions may be made by from the system 100 pertaining to optimal next steps in the delivery of the instrument (102) or therapy to a target based on the training library 142 of similar clinical cases with corresponding instrument manipulation archive recordings and clinical outcomes. A guidance module or system 146 may be included to provide verbal, visual, graphical, acoustic or other feedback to a trainee or physician during a session using an output mechanism 152. The guidance module 146 includes programs that compare the real-time data being received with a model (e.g., a statistical model) of the proper actions from database 140 or from best practices from database 144 and alerts the user of any deviation that is beyond a set threshold. For example, if the user goes down a wrong path the guidance module 146 would alert the user with a warning signal (light or sound), a message (e.g., "you are out of position"), a graphic on the display 118 showing a proper path, etc.

Figure 2:
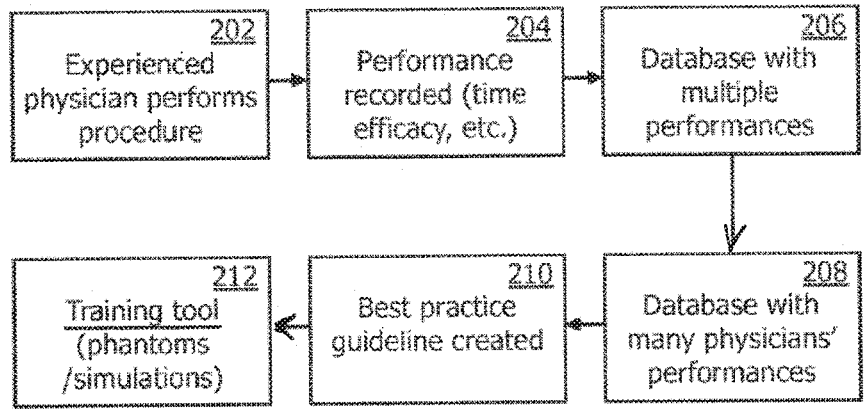
FIG. 2 is a block/flow diagram showing creation of a training tool using data stored during expert actions using the system in accordance with one embodiment.

Referring to FIG. 2, a training workflow is illustratively described to train a database for the creation of a training tool or rating tool in accordance with one embodiment. In block 202, one or more experienced physicians perform one or more different operative procedures. During the procedure(s), the physician's activities are monitored through the recording of shapes or poses of a shape sensing enabled instrument or instruments and stored in a database. In block 204, the results of each performance are recorded and associated with the performance data in the database. The results may include a subjective or objective assessment of the procedure to provide a measure of the desirability of the worksteps and their execution. In block 206, the database is populated with multiple performances of the experienced physician and the results for a given procedure so that statistical data may be accumulated and acceptable/not acceptable criteria can be discovered and employed for that procedure. In block 208, the database is populated with multiple performances of many experienced physicians and their results so that statistical data may be accumulated and acceptable/not acceptable criteria can be discovered and employed. Blocks 206 and 208 may be adjusted as needed. For example, a single physician may be employed as the benchmark for a training session or an entire population of physicians may be employed.

In block 210, best practice criteria may be created. This may include adding local inputs (e.g., hospital procedures and the like) as well as identifying and employing acceptable/not acceptable criteria from blocks 206 and 208. This may include creating models for comparison to real-time training data to determine whether a trainee is qualified or to provide a rating for a physician, etc. In block 212, the models and data are combined to create a training tool. The training tool may include simulations or graphical interfaces where the user controls the shape sensing enabled device in a physical model or a simulated virtual model (e.g., using medical images of an anatomy). The interface control data can be matched with the data or models to evaluate the user's performance. The training tool may be employed in different scenarios. Two examples will be illustratively described with reference to FIGS. 3 and 4.

Figure 3:
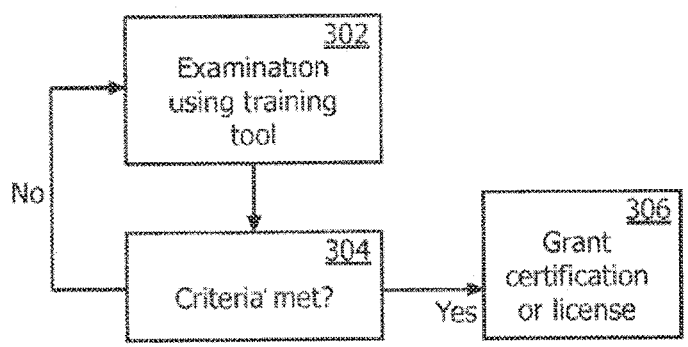
FIG. 3 is a block/flow diagram showing an example workflow for employing the system/tool of FIG. 1 to certify a user in accordance with one embodiment.

Referring to FIG. 3, a trainee, such as a medical student or inexperienced physician, may employ the training tool as an examination system. In block 302, an examination is performed by simulating a procedure using the training tool. The trainee's movements are evaluated against the database and models of the training tool to determine the trainee's competency. In block 304, a determination is made as to whether the trainee met the goals and execution criteria. If the goals and criteria are met, in block 306, the trainee may become licensed or certified to perform the procedure. Otherwise, the trainee must practice and retake the examinations in block 302.

Figure 4:
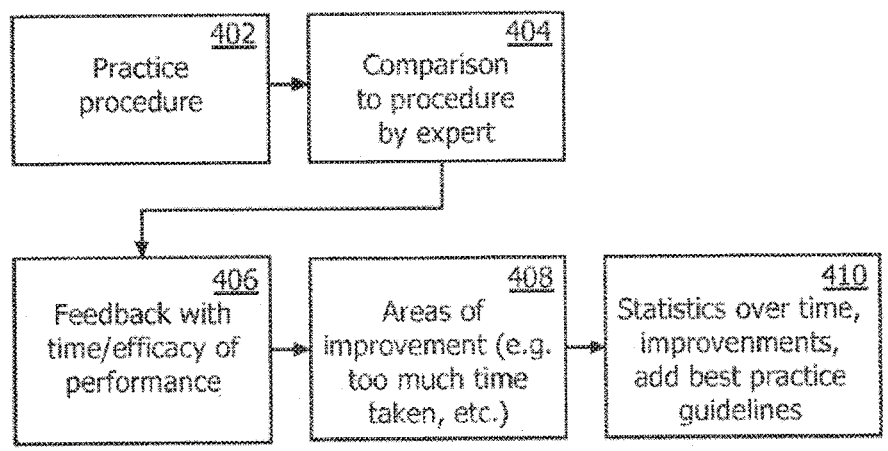
FIG. 4 is a block/flow diagram showing another example workflow for employing the system/tool of FIG. 1 to teach the user how to appropriately perform one or more procedures and to further train the system/tool in accordance with one embodiment.

Referring to FIG. 4, another illustrative workflow is described which employs the training tool created in FIG. 2. In block 402, a physician untrained in a procedure practices the procedure using the training tool. In block 404, the training tool compares real-time feedback from the practiced procedure against its expert physician models. This includes finding similarities and differences in the execution using the shape sensing enabled device or devices. In block 406, feedback is presented/reported to the physician or testing authority with time, efficacy, and other metrics. In block 408, the system presents areas of improvement (e.g., too much time spent on a particular portion of the procedure, etc.). In block 410, statistics may be gathered over time for the inexperienced physician to show or demonstrate improvements. In addition, the collected data may be employed to supplement the database and/or the best practice guidelines.

Figure 5:
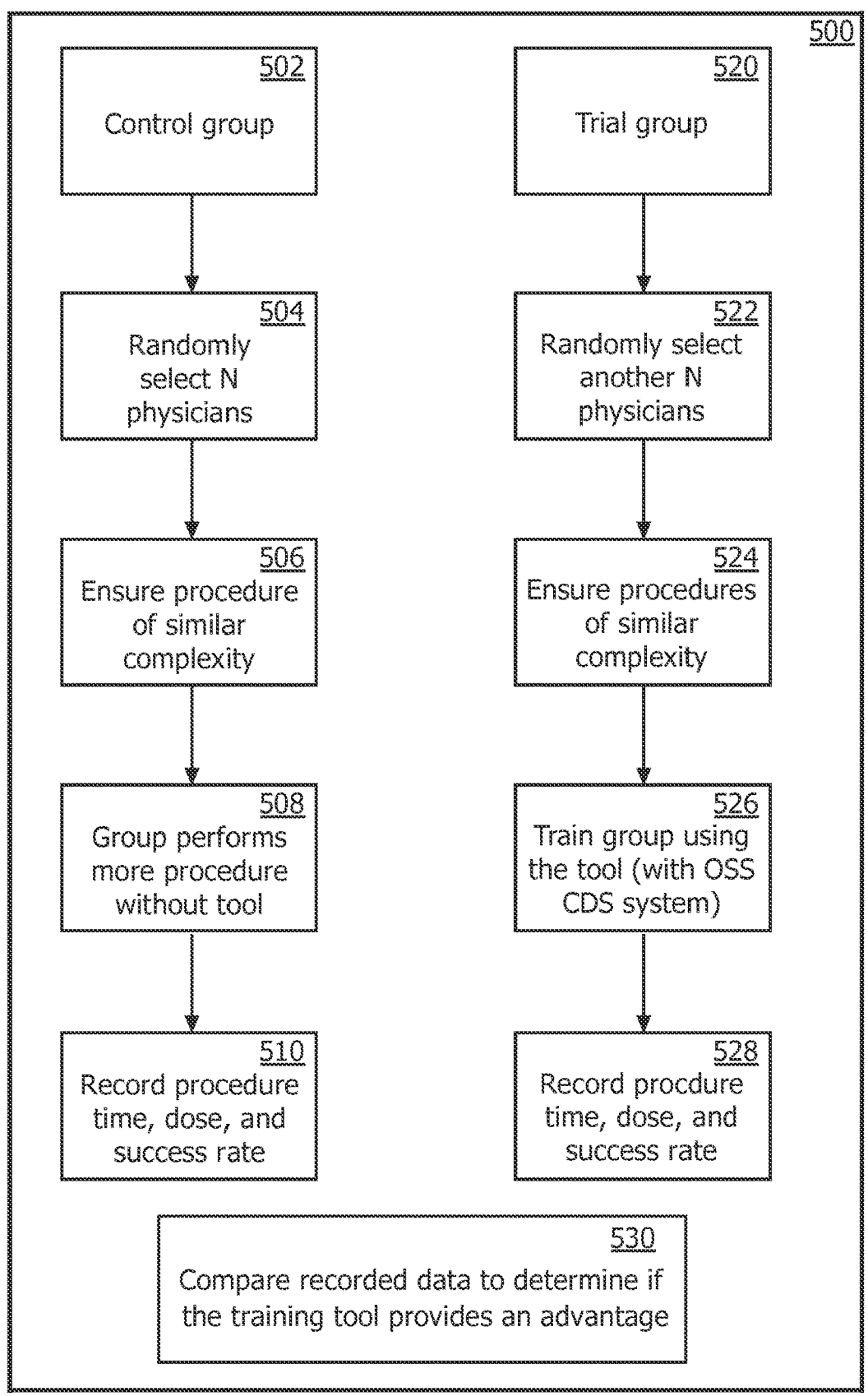
FIG. 5 is a block/flow diagram showing an example workflow for conducting an illustrative study to determine the effectiveness of using the system/tool of FIG. 1 in accordance with one embodiment.

Referring to FIG. 5, another illustrative workflow is described for conducting an experimental study to determine evidence for procedure changes using the training tool created in FIG. 2. In block 500, an illustrative experimental study includes a control group 502 and a trial group 520. In block 504, the control group includes a set of N randomly selected physicians. In block 506, the procedure being studied is analyzed to determine whether the complexity is similar to that of the trial group (in block 524). In block 508, the control group performs the surgery without employing the tool or system 100. In block 510, metrics such as time, dose, success rate, etc. are recorded for the control group.

In block 522, the trial group includes another set of N randomly selected physicians (different from the control group). In block 524, the procedure being studied is analyzed to determine whether the complexity is similar to that of the control group (in block 506). In block 526, the trial group employs the training tool in accordance with the present principles. This may include the use of the guidance system for assistance, being trained and rated/certified, etc. In block 528, metrics such as time, dose, success rate, etc. are recorded for the trial group. In block 530, a comparison is performed to understand whether training with the training tool provides a statistical advantage to the physicians trained with the training tool over the physicians trained without the training tool. Other studies may be conducted using the training tool.

Figure 6:
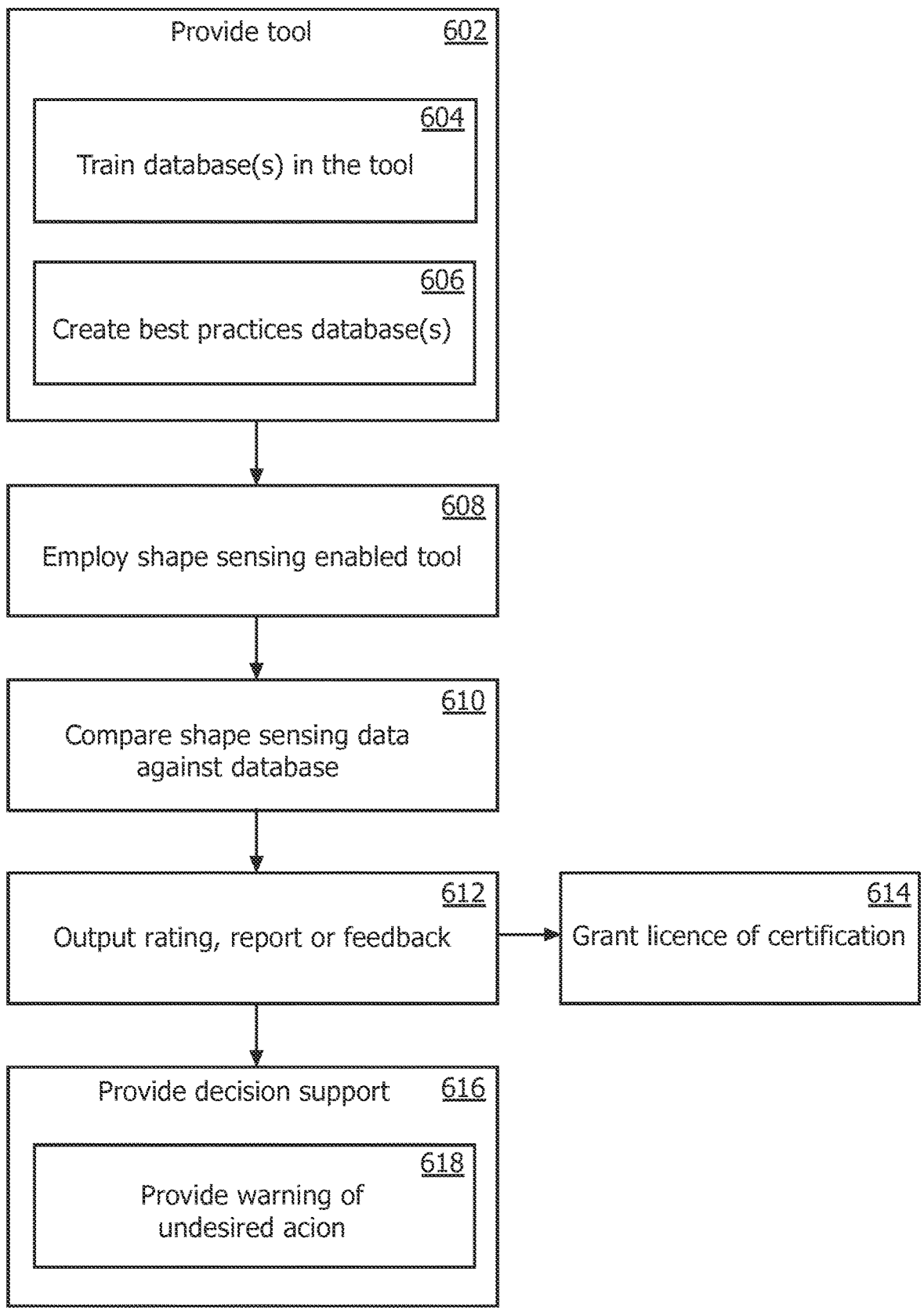
FIG. 6 is a flow diagram showing a method for training and/or decision support using the system/tool of FIG. 1 in accordance with the present principles.

Referring to FIG. 6, a method for procedural training and/or decision support is illustratively shown in accordance with the present principles. In block 602, a training/decision support tool (100) is provided. The system may include trained databases having a plurality of procedures and/or plurality of experts performing the procedures stored therein. The database may include libraries of data related to a procedure type or types, a physician(s) and a particular circumstance or circumstances (e.g., anatomical limitations, e.g., removed organs etc.) for the procedure. Performance information may include shapes of medical instruments that occur during a given procedure. In block 604, the database may be trained using data collected from one or more experts appropriately performing the procedure.

In block 606, a best practices database may be created that may include procedure specific constraints or environment specific constraints. These constraints may be outside the appropriate procedure data, e.g., local laws, hospital rules etc.

In block 608, a trainee, a less experienced user or any user may employ a shape sensing enabled device under simulated or actual conditions. The shape sensing enabled device preferably includes an optical fiber shape sensing device, or other device to collect shape data for comparison to the best practices database or other criteria or standards. It should be understood that while a single shape sensing device is described, it may be the case that several devices may be employed concurrently and be part of the training and or rating/comparison performed.

Simulated conditions may include a virtual usage of the device while actual conditions may be on a live patient, a cadaver or in an anatomical model. In block 610, usage of the shape sensing enabled device is compared against a database of possible shapes and sequences of shapes for the shape sensing enabled device (e.g., a trained database). The possible shapes and sequences of shapes may include a collection of poses derived by appropriately performing a procedure with the shape sensing enabled device. In other words, the experts in the database are preferably the standard with which the present user will be compared. The comparison may be done based on time segments, based on worksteps, based on performance metrics or based on the procedure as a whole.

In one example, the number and type of bends undergone by a segment of the shape sensing enabled device may be employed as comparison criteria. In another embodiment, the path taken by the shape sensing enabled device may be employed as comparison criteria. In another embodiment, the path taken by the shape sensing enabled device in a given period of time may be employed as comparison criteria. In still another embodiment, the path taken by the shape sensing enabled device to reach a target position may be employed as comparison criteria. Other criteria and combinations of these and other criteria may also be employed.

In block 612, a rating or improvement feedback is output based on a comparison of real-time poses of the shape sensing enabled device with the collection of poses in the database. The output may take many forms and may include, e.g., a probable outcome of the procedure performed by the user, an execution time for procedure steps; a rating number, e.g., from 1-10, etc.

In block 614, based on the feedback of a user performance a certification or license may be granted to permit the user to perform this procedure under actual conditions, etc. In block 616, information may be provided to a user to assist the user in determining a course of action during the procedure. This information may be in the form of decision support to assist the user in making a decision that follows a majority of the experts (e.g., the information is based upon the collection of poses derived by appropriately performing the procedure) or other decision support criteria. In one embodiment, a warning may be issued to the user of an undesirable action during the procedure in block 618. The warning may include an audible, haptic or visual warning.

In interpreting the appended claims, it should be understood that:
a) the word "comprising" does not exclude the presence of other elements or acts than those listed in a given claim;
b) the word "a" or "an" preceding an element does not exclude the presence of a plurality of such elements;
c) any reference signs in the claims do not limit their scope;
d) several "means" may be represented by the same item or hardware or software implemented structure or function; and
e) no specific sequence of acts is intended to be required unless specifically indicated.

Having described preferred embodiments for clinical decision support and training system using device shape sensing (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A rating system configured for utilization of an actual elongated medical device for intracorporeal intervention, at least a portion of said elongated medical device being capable of being manipulated into different shapes intracorporeally, said rating system being configured to rate a performance of manipulating said portion of said elongated medical device during a procedure, said system comprising:
 a shape sensing system that includes a plurality of sensors configured for sensing actual shapes of said portion of said elongated medical device at various times during a performance of the procedure and for outputting feedback indicating the actual shapes of said portion of said elongated medical device during the performance of the procedure, the plurality of sensors including a plurality of fiber optic Bragg grating sensors or a plurality of electromagnetic tracking devices distributed along a length of said portion of said elongated medical device;
 a database of possible shapes and sequences of shapes of said portion of said elongated medical device, the possible shapes and sequences of shapes including a collection of poses derived by appropriately performing the procedure with said elongated medical device, wherein the possible shapes are stored in the database as a collection of (x, y, z, t) coordinates for a plurality of points along a length of the portion of said elongated medical device specifying (x, y, z) positions of the points at given times t when appropriately performing the procedure; and
 a processor comprising:
  a) a shape sensing module configured for interpreting the feedback from said sensors of said shape sensing system to derive the actual shapes of said portion of said elongated medical device during the performance of the procedure; and
  b) a comparison module configured to compare said actual shapes with the possible shapes in the database and in response to said comparison, to output a numerical score for the performance of the procedure.

2. The system of claim 1, wherein said database includes data collected from one or more experts appropriately and actually performing said procedure by actually manipulating said elongated medical device.

3. The system of claim 1, further comprising said elongated medical device, wherein said elongated medical device includes at least one of the plurality of fiber optic Bragg grating sensors and the plurality of electromagnetic tracking devices.

4. The system of claim 1, wherein the database further includes a best practices database, which includes procedure specific constraints or environment specific constraints.

5. The system of claim 1, wherein the database further includes libraries of data related to a procedure type, a physician and a particular circumstance for the procedure typed.

6. The system of claim 1, further comprising a user-output mechanism, and wherein said processor further comprises an interactive guidance module configured to provide, via said user-output mechanism, information to a user of the rating system to assist said user in determining a course of action during the performance of the procedure.

7. The system of claim 6, wherein said information provided by said interactive guidance module is based upon said collection of poses derived by appropriately performing said procedure.

8. The system of claim 6, wherein said user-output mechanism comprises a display, and wherein said providing includes displaying via said display.

9. The system of claim 1, wherein said database stores the collection of poses associated with procedure outcomes, and said comparison module is configured to output a probable outcome of the performance of the procedure that is being rated.

10. The system of claim 1, wherein said procedure comprises a plurality of steps, and wherein said comparison module is configured to compare execution times for said steps during the performance of the procedure to execution times for said steps in the database for appropriately performing the procedure.

11. The system of claim 1, wherein said portion is a functional end of said elongated medical device.

12. The system of claim 1, further comprising a display said processor is configured for operating to visualize, on said display, feedback from among said comparison module to said user for performing the procedure interactively.

13. A system configured to rate at least one of a virtual user performance and an actual user performance of a procedure by a user of the system, said system comprising:
a shape sensing system that includes one of: (1) a plurality of virtual sensors; and (2) a plurality of actual sensors configured for correspondingly sensing virtual shapes or actual shapes of at least a portion of a corresponding one of: (1) a virtual elongated medical device, and (2) an actual elongated medical device, during the virtual user performance or actual user performance of the procedure and for outputting feedback indicating the virtual shapes or actual shapes of said portion of said virtual elongated medical device or actual elongated medical device at various times during the virtual user performance or actual user performance of the procedure;
a database of possible sequences of shapes of said portion of said virtual elongated medical device or actual elongated medical device, the possible sequences of shapes including a collection of poses derived by appropriately performing the procedure with said virtual elongated medical device or actual elongated medical device, the possible sequences of shapes each being stored in the database as a sequence of collections of (x, y, z, t) coordinates for a plurality of points along a length of the portion of said virtual elongated medical device or actual elongated medical specifying (x, y, z) positions of the points at given times t when appropriately performing the procedure; and
a processor comprising:
a) a shape sensing module configured for interpreting the feedback signals from said shape sensing system to derive the virtual shapes or actual shapes of said portion of said elongated medical device during the virtual user performance or actual user performance of the procedure;
b) a comparison module configured to compare a sequence of the virtual shapes or actual shapes of said portion of said elongated medical device during the virtual user performance or actual user performance of the procedure with the possible sequences of shapes in said database and in response to said comparison to output a rating of said virtual user performance or actual user performance of the procedure.

14. The system of claim 13, wherein said database further includes at least one of (i) data collected from one or more experts appropriately performing the procedure, (ii) a best practices database, which includes procedure specific constraints or environment specific constraints, and (iii) libraries of data related to a procedure type, a physician and a particular circumstance for the procedure type.

15. The system of claim 13, further comprising said actual elongated medical device, and said shape sensing system includes said plurality of actual sensors, wherein the plurality of actual sensors includes a plurality of fiber optic Bragg grating sensors or a plurality of electromagnetic tracking devices.

16. The system of claim 13, further comprising a user-output mechanism, and wherein said processor further comprises an interactive guidance module configured to provide guidance to a user during the performance of the procedure, whereon the guidance comprises information based upon the collection of poses derived by appropriately performing the procedure,
wherein said database stores said collection of poses associated with procedure outcomes such that said system outputs via the user-output mechanism a probable outcome of said virtual user performance or said actual user performance of the procedure,
wherein said user-output mechanism provides said rating and said indication of the probable outcome through one or more of visual, acoustic and graphical modes, and
wherein the user-output mechanism is further configured to provide a warning message for an undesirable action during said virtual user performance or said actual user performance of the procedure.

17. The system of claim 13, further comprising a user interface that includes a control operable by a user of correspondingly the virtual elongated medical device or the actual elongated medical device to correspondingly, in the virtual user performance or actual user performance of the procedure, virtually or actually manipulate said virtual elongated medical device or actual elongated medical device into a different current shape of said virtual elongated medical device or actual elongated medical device,
wherein said control is operable for said actual user performance of the procedure, said shape sensing system includes said multiple actual sensors, said guided user performance is actual, and said actual device includes at least one of the optical-fiber shape-sensing device and electromagnetically tracked device.

18. A non-transitory computer readable medium embodying a computer program for at least one of procedural training and decision support, said program including instructions executable by a processor for performing a plurality of acts, from among said plurality there being the acts of:
sensing by one of: (1) a plurality of virtual sensors, and (2) a plurality of actual sensors, during a simulated performance or actual performance of a procedure, virtual shapes or actual shapes of at least a portion of a corresponding one of: (1) a virtual elongated medical device, and (2) an actual elongated medical device, during the virtual user performance or actual user performance of the procedure and for outputting feedback indicating the virtual shapes or actual shapes of said portion of said virtual elongated medical device or actual elongated medical device at various times during the virtual user performance or actual user performance of the procedure;
deriving, based on sensor output from said sensing, the virtual shapes or actual shapes of said portion of said virtual elongated medical device or actual elongated medical device during the virtual user performance or actual user performance of the procedure;
comparing a sequence of the virtual shapes or actual shapes of said portion of said virtual elongated medical device or actual elongated medical device during the virtual user performance or actual user performance of the procedure against a database of possible sequences of shapes of said portion of said virtual elongated medical device or actual elongated medical device including a collection of poses derived by appropriately performing the procedure with said virtual elongated medical device or actual elongated medical device, the possible sequences of shapes being stored in the database as a sequence of (x, y, z, t) coordinates for a plurality of points along a length of the portion of said virtual elongated medical device or actual elongated medical specifying (x, y, z) positions of the points at given times t when appropriately performing the procedure; and
outputting, based on the comparison, a rating of said virtual user performance or actual user performance of the procedure.

19. The computer readable medium of claim 18, wherein said comparing further includes accessing from said database a shape from among said possible sequences of shapes and computing a metric descriptive of a difference in point positions between one of said virtual shapes or said actual shapes of said virtual elongated medical device or actual elongated medical device, and the accessed shape, and wherein the rating is based on said metric.

20. The computer readable medium of claim 18, wherein said comparing further includes: computing a number and type of bends currently undergone by said virtual elongated medical device or actual elongated medical device; accessing from said database a number and type of bends undergone by correspondingly said virtual or actual device when appropriately performing the procedure; and comparing the computed number and type to the accessed number and type.

21. The computer readable medium of claim 18, wherein said comparing further includes: computing a path currently taken by said virtual elongated medical device or actual elongated medical device; accessing from said database a path taken by said virtual elongated medical device or actual elongated medical device when appropriately performing the procedure; and comparing the computed path to the accessed path, and wherein the rating is based on the comparison between the computed path and the accessed path.

22. The computer readable medium of claim 18,
wherein said comparing includes: computing a number of different shapes that are derived based on said sensor output and into which said device is manipulated as a result of said virtual user performance or actual user performance; accessing from the database a number of possible shapes of said elongated medical device or actual elongated medical device; and comparing the computed number of shapes to the accessed number of shapes, and
wherein the rating is based on the comparison between the computed number of shapes and the accessed number of shapes.

* * * * *